United States Patent [19]

Hill et al.

[11] 4,373,532
[45] Feb. 15, 1983

[54] ULTRASONIC MARKER FOR PHYSIOLOGIC DIAGNOSIS AND METHOD OF USING SAME

[75] Inventors: Bruce C. Hill; Roger A. Stern, both of Palo Alto, Calif.

[73] Assignee: Palo Alto Medical Research Foundation, Palo Alto, Calif.

[21] Appl. No.: 166,556

[22] Filed: Jul. 7, 1980

[51] Int. Cl.³ ............................................... A61B 10/00
[52] U.S. Cl. .................................... 128/660; 128/661; 128/663
[58] Field of Search ......................... 128/630, 653–654, 128/659–663, 691–692, 694, 774, 335.5, 24 A, 349 R; 3/1, 4; 73/861.25

[56] References Cited

U.S. PATENT DOCUMENTS 4,010,759 3/1977 Baer .................................. 128/419 P Primary Examiner—Kyle L. Howell
Assistant Examiner—F. Jaworski
Attorney, Agent, or Firm—Julian Caplan

[57] ABSTRACT

For non-invasive diagnosis of conditions subsequent to a medical operative procedure, at the time of operation a "target" is sutured to tissue. Later, by use of an ultrasonic imaging system or other diagnostic instrument, the location of the target can be accurately determined. Thereupon, non-invasive techniques may be used in the target area to determine changes in physiology subsequent to implanting the target. For example, a target consisting of a fused array of small stainless steel balls is sutured to a coronary artery bypass graft. Later, to determine if the bypass graft is patent, by ultrasonic methods the location of the target and hence the bypass graft is determined. Then, using a Doppler-effect flowmeter, flow through the bypass graft may be measured and compared with prior measurements. The marking technique is also believed to be useful in postoperative determination of tumor growth at the locus of said marker.

6 Claims, 8 Drawing Figures

ULTRASONIC MARKER FOR PHYSIOLOGIC DIAGNOSIS AND METHOD OF USING SAME

This invention relates to a new and improved marker for medical diagnosis and to a method of using the same.

Heretofore, ultrasonic scanning has been used to image areas of the anatomy, especially of the heart. However, localization and positive identification of small structures by such scanning has not heretofore been practical. One such structure is an arterial bypass graft. A preferred use of the present invention is in the localization of an arterial bypass graft to detect whether there is blood flow through said graft. Such detection by ultrasonic or other non-invasive techniques has been impractical heretofore.

Ultrasonic scanning has been used heretofore to detect flow in large blood vessels (such as the aorta) by means of the Doppler effect. However, it is necessary to aim the transducer very accurately and such accuracy has not consistently been achieved heretofore in areas such as a coronary artery bypass graft because locating and identifying such a small structure has been largely fortuitous.

Accordingly, the present invention provides a means whereby ultrasonic scanning may be accurately and consistently directed at a specific area of tissue. Such accurate scanning makes it possible, for example, to measure flow through a bypass graft by ultrasonic means.

At the time of surgery, a target is implanted in the tissue at a critical area. Subsequently, the target may be used as a means to precisely direct the transducer of an ultrasonic imaging system or to direct another diagnostic instrument. Hence, changes at the locus of the target may be determined.

One of the features of the invention is the fact that after the initial surgery, no invasive techniques are required to make such determinations. Invasive techniques such as coronary arteriography require hospitalization, pain, and discomfort and there is danger of injury to the patient and even mortality.

The present invention requires less expensive equipment than coronary arteriography and involves no danger to the patient.

One of the features of the invention is the provision of a target which is simple and relatively inexpensive and permanent so that it remains at the locus of its initial implantation.

A preferred target is a planar array of stainless steel balls of small diameter which are welded or otherwise fused together. Such a target may be sutured to the tissue very conveniently.

One of the advantages of the target previously mentioned is that the balls reflect ultrasonic beams incident at any angle. Furthermore, the target provides a characteristic ultrasonic image which aids in its identification: namely, a reverberatory pattern in the ultrasonic scan which differs from the image of surrounding native tissue. The telltale "signature", a reverberatory pattern, has a tail which is aligned with the direction of the beam and hence is extremely useful in interpretation of the ultrasonic image.

A preferred use of the invention is in the determination of blood flow through a coronary artery bypass graft at any time after the implantation. In accordance with a preferred form of the invention, a target heretofore described is sutured to the vein used as a bypass graft and remains permanently in place. When flow through the bypass graft is to be determined, the target is utilized to indicate that the ultrasonic beam is directed toward the vein implant in question. Thereupon, by standard Doppler ultrasonic techniques the velocity of blood flow through the area may be determined.

The present invention has been used successfully in implantations on arteries of dogs with highly satisfactory results. In addition to determination of blood flow, the present invention is believed to be useful in determining changes in the condition of a tumor, e.g., by implanting the target in an area of a tumor and then subsequently assessing tissue changes around the marker, growth or shrinkage of the tumor may be determined. It is believed that the present invention has many other uses where precise aiming of an ultrasonic sector scan and unambiguous identification of specific anatomical structures and regions of tissue are desirable.

Other objects of the present invention will become apparent upon reading the following specification and referring to the accompanying drawings in which similar characters of reference represent corresponding parts in each of the several views.

Figure 1:
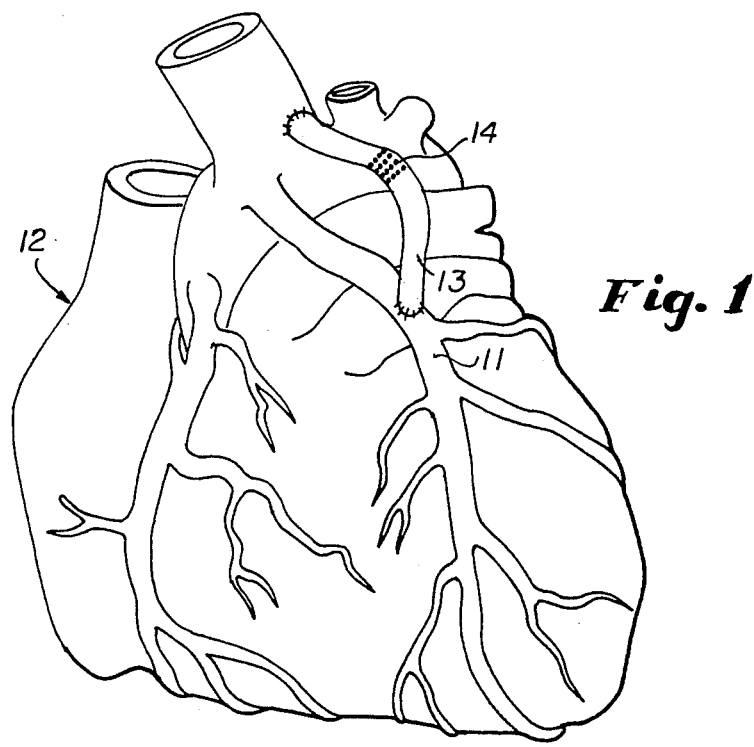
FIG. 1 is a schematic perspective view of the heart and coronary arteries showing a bypass graft having a marker in accordance with the present invention sutured to the implant.

As has been stated, the present invention is useful and is believed to be potentially useful in a variety of environments where it is necessary to aim precisely a beam of ultrasonic energy. One preferred use of the present invention is in the determination of flow through a coronary bypass graft at a time subsequent to the original surgery. Directing attention to FIG. 1, there is shown a coronary artery 11 on the heart 12. A bypass graft 13 (typically a vein) has been grafted to the artery 11. All of these procedures are well known. However, determination of whether the bypass graft 13 is patent at a time subsequent to the original surgery has been an extremely important problem.

In accordance with the present invention, a marker 14 is sutured to the graft 13. The marker 14 remains permanently in place.

Figure 2:
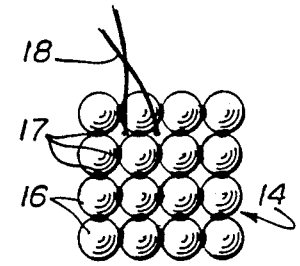
FIG. 2 is a schematic view showing in enlarged scale a target in accordance with the present invention during a medical operative procedure at the commencement of suturing the marker to tissue.
Figure 3:
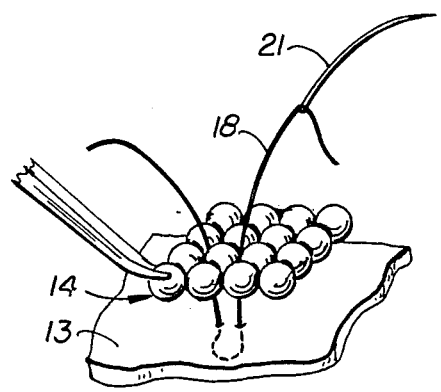
FIG. 3 is a perspective view showing the operation of FIG. 2 from a different angle.
Figure 4:
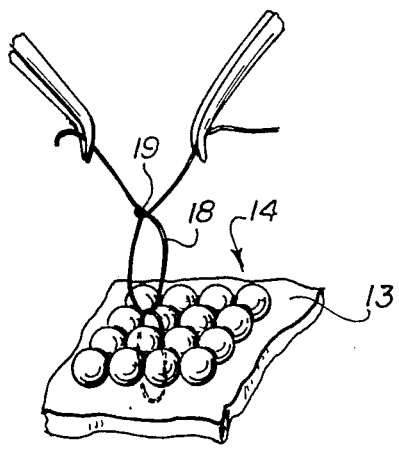
FIG. 4 shows the tying of a knot in the suture, firmly affixing the target to the desired tissue.

Directing attention to FIGS. 2-4, marker 14 is preferably an array of small stainless steel balls 16 in a flat or planar configuration. In a preferred form shown in FIGS. 2-4 there are sixteen stainless balls 16 of about 1/16″ diameter which are joined together at their tangent points in welds 17, preferably in columns and rows of four. In another preferred target (not shown) four balls in a 2×2 array is used. The marker or target 14 may be secured to the tissue 13 by suture material 18. The needle 21 is brought down through the interstices between four balls 16 and through the outer layer of tissue of the graft 13 as best shown in FIGS. 2 and 3. Thereupon, by conventional surgical techniques, the suture material 18 is formed in a knot 19 which secures the target in place. Several sutures may be used as required. It will be understood that the number of balls 16 and the pattern thereof is subject to considerable variation. Further, although the use of welded balls is preferred at present, it will be understood that other metallic or non-metallic markers 14 may be used. One of the advantages of the balls shown herein is that they have the effect of a characteristic reverberatory pattern in the ultrasonic image which aids in identification.

Figure 5:
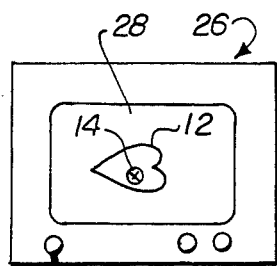
FIG. 5 is a schematic view showing the use of an ultrasonic instrument on a patient at any time subsequent to the implantation of the marker.
Figure 5:
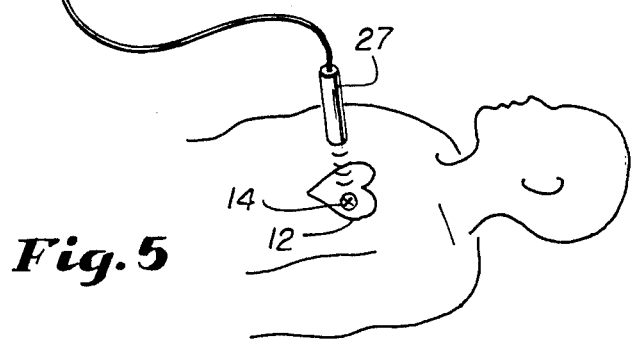

Directing attention now to FIG. 5, the procedure which is followed at some time subsequent to the implantation of the marker 14 is illustrated. Commercially available equipment is used. One suitable device is the Picker Echocardiographic System 80C 1 manufactured by Picker Corporation of Northford, Conn. Another suitable device is Ekosector System I of Smith, Kline. Still another is the Mark V duplex scanner of Advanced Technology Laboratories, Inc., of Bellevue, Washington; other equipment is suitable. Attached to such a device 26 is an ultrasonic transducer 27. A video display 28 shows a sector scan produced by the transducer 27. It is noted that the transducer is at the surface of the skin and the scan is preferably through a "window" in the body which allows passage of ultrasonic energy unblocked by bones, lung, etc. Thus, for a coronary bypass graft determination, a window in the chest wall such as between the ribs or through the suprasternal notch may be used. The marker 14 is so placed as to be accessible to ultrasonic imaging through these windows. In a typical example, location of the marker 14 near the aorta is suitable.

Figure 6:
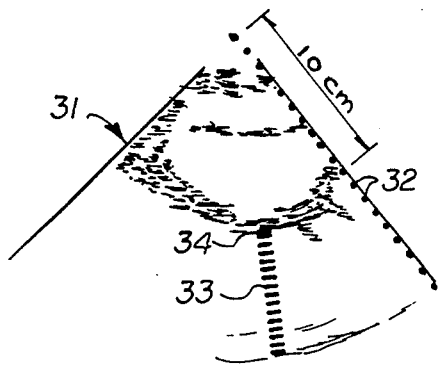
FIG. 6 is a schematic rendition of an actual sector scan of the heart of a dog showing the marker which had previously been sutured to the heart and its characteristic reverberatory "signature".

A typical sector scan 31 as observed on the video display 28 is shown in FIG. 6. The lines on the drawing represent tissue boundaries. Along one or more edges of the sector are equally spaced marks 32 which indicate the depth from the skin where the various anatomical structures are located. The representation 34 of marker 14 may be obscured by its proximity to other tissue. However, as is particularly important in the present invention, the marker representation 34 by reason of echo reverberations 33 displays a telltale series of short lines in the form of a tail. Another important feature is the fact that the tail is always aligned along the direction of the incident ultrasonic beam. The ultrasonic beam impinging upon the maker may produce a signal which is a reflection of said beam, or a scattering thereof, or a transmission thereof, all of which are distinguishable from the signals produced by tissue adjacent the marker.

Figure 7:
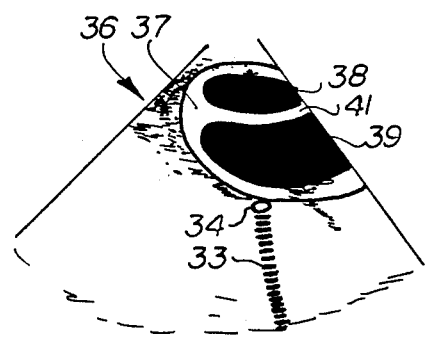
FIG. 7 is a schematic rendition of the results of FIG. 6 showing the tissue surrounding the marker and specifically identifying the areas of the heart imaged and also showing the reverberatory signature.

The schematic illustration 36 of FIG. 7 is an interpretation of what is shown in FIG. 6. Thus, the heart wall is shown as reference numeral 37 and within the wall are the right ventricle 38 and the left ventricle 39 separated by the septum 41. Again, the marker representation 34 and the reverberatory signature 33 are displayed. By such means the marker representation 34 is located and hence the location of marker 14 and the anatomical structure of interest is determined.

Figure 8:
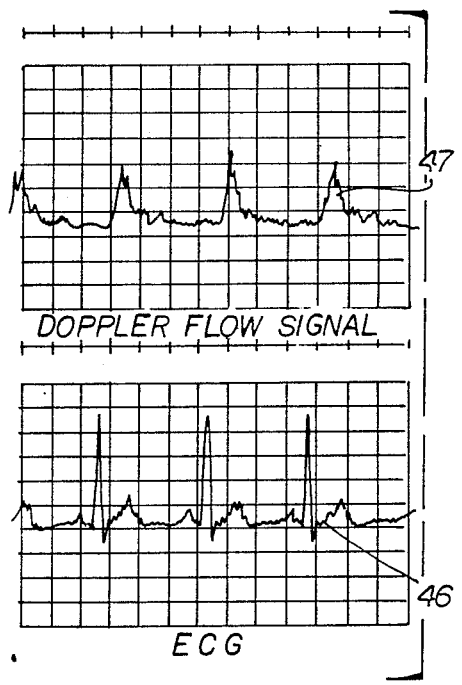
FIG. 8 shows portions of a (strip-chart) recording which may be made after aiming the ultrasonic transducer on the marker showing the Doppler velocity signals which indicate flow through the vessel in the region of the marker. (An electrocardiographic signal as an aid to identifying the time course of cardiac events is also shown.)

The Mark V instrument mentioned above has a further feature in that by the Doppler effect a characteristic blood flow signal 47 may be displayed on a recording as illustrated in FIG. 8. If an ECG is displayed on the same or a closely parallel recording, as illustrated by reference numeral 46, the flow through the bypass graft 13 where the marker 14 is located may be compared to other events in the cardiac cycle.

As used herein, the term "animal" includes humans.

What is claimed is:

1. A marker for ultrasonic diagnosis comprising a body which provides, upon being subjected to a beam of ultrasonic energy, a reflected, transmitted or scattered acoustic signal distinct from the signal produced by surrounding tissue and means for chronically securing said marker to animal tissue for implantation during surgery, said body comprising an array of balls tangent to a plurality of adjacent balls and attached at the points of tangency, said balls being metallic and fused to each other.

2. A marker according to claim 1, in which said body is substantially planar.

3. A marker according to claim 1 in which said attachment means for securing comprises the interstices between said balls through which a surgical needle and suture may pass.

4. A method of non-invasive, post-operative diagnosis of conditions at the locus of an anatomical structure not having ultrasonic characteristics distinguishable from adjacent structure, comprising performing an incision and medical operative procedure at said locus, implanting an ultrasonically detectable marker to tissue at said locus, and subsequently aiming by means of an ultrasonic diagnostic instrument an ultrasonic transducer beam in the region of said marker and recording on the screen of said instrument the image of said marker, thereby indicating said locus, said marker, upon being subjected to a beam of ultrasonic energy reflecting, scattering or transmitting an acoustic signal distinguishable from the signal produced by surrounding anatomical structure, said marker comprising a planar array of balls joined at their tangencies and in which the screen of said instrument shows a reverberatory pattern signature which indicates the direction and depth of said marker.

5. The method of claim 4, which further comprises obtaining a Doppler-shift flowmeter analysis of blood flow in the region of said marker.

6. The method of claim 4, in which said operative procedure is an artery bypass graft operation and said marker is sutured to said graft and which further comprises obtaining Doppler-shift analysis of blood flow at said marker and thereby determining whether said graft is patent.

* * * * *